(12) United States Patent
Abeysekara et al.

(10) Patent No.: US 11,185,434 B2
(45) Date of Patent: Nov. 30, 2021

(54) SUPPORT AND COMPRESSION GARMENTS

(71) Applicants: Carolyn Joy Taylor, Victoria (AU); AUSTRIMM PTY LTD, Victoria (AU)

(72) Inventors: Michel Abeysekara, Glen Iris (AU); Carolyn Joy Taylor, Victoria (AU); Fiona Green, Brunswick (AU); Wendy Reynolds, Ascot Vale (AU)

(73) Assignees: KEMAJE PTY.LTD, Melbourne (AU); Carolyn Joy Taylor, Melbourne (AU)

( * ) Notice: Subject to any disclaimer, the term of this patent is extended or adjusted under 35 U.S.C. 154(b) by 0 days.

(21) Appl. No.: 15/135,910

(22) Filed: Apr. 22, 2016

(65) Prior Publication Data

US 2016/0235576 A1 Aug. 18, 2016

Related U.S. Application Data

(63) Continuation of application No. 13/184,852, filed on Jul. 18, 2011, now abandoned.

(51) Int. Cl.
*A61F 5/02* (2006.01)
*A41B 9/14* (2006.01)
(Continued)

(52) U.S. Cl.
CPC ............... *A61F 5/028* (2013.01); *A41B 9/14* (2013.01); *A41D 1/089* (2018.01);
(Continued)

(58) Field of Classification Search
CPC ........ A41D 1/08; A41D 1/20; A41D 13/0015; A41D 13/0506; A41D 13/0525;
(Continued)

(56) References Cited

U.S. PATENT DOCUMENTS 1,281,538 A    10/1918   Dupuy
2,239,972 A  *   4/1941   Rauser ..................... A41B 9/02
                                                2/234
(Continued)

FOREIGN PATENT DOCUMENTS

AU    2010200001 A1   7/2010
CA      2584636 A1   4/2006
(Continued)

OTHER PUBLICATIONS

Website Printout: "Compression Technology", SKINS International (2 Pages).

(Continued)

*Primary Examiner* — Jameson D Collier
(74) *Attorney, Agent, or Firm* — Dilworth & Barrese, LLP

(57) ABSTRACT

A support and compression garment (10) including a body (11) having at least one support and compression portion (32) for providing support and compression to at least one targeted region of a person's body and at least one support and compression member (70) associated with the at least one support and compression portion (32) for increasing the amount of support and compression. Garment (10) may have a plurality of support and compression portions, and the level of support and compression by the portions may be varied as desired.

10 Claims, 11 Drawing Sheets

(51) Int. Cl.
*A41C 1/10* (2006.01)
*A41D 1/089* (2018.01)
*A41D 13/00* (2006.01)
*A41D 31/18* (2019.01)
*A41C 1/00* (2006.01)

(52) U.S. Cl.
CPC ......... *A41D 13/0015* (2013.01); *A41D 31/18* (2019.02); *A41C 1/003* (2013.01); *A41C 1/10* (2013.01)

(58) Field of Classification Search
CPC ............ A41D 13/0537; A41D 2300/22; A41D 2400/38; A41B 9/04; A41B 9/14; A41B 2400/38; A61F 5/028; A41C 1/08; A41C 1/10; A41C 3/08; A41C 1/003
USPC ......... 2/78.1, 78.3, 229, 236, 237, 400–404, 2/406, 407
See application file for complete search history.

(56) References Cited

U.S. PATENT DOCUMENTS

| | | | |
|---|---|---|---|
| 2,310,864 A | 2/1943 | Pegg | |
| 3,083,710 A | 4/1963 | Rauser | |
| 3,312,981 A * | 4/1967 | McGuire | A61F 13/72 2/406 |
| 3,339,554 A | 9/1967 | Nobbs | |
| 3,393,675 A | 7/1968 | Trznadel et al. | |
| 3,396,730 A | 8/1968 | Fox | |
| 3,601,130 A * | 8/1971 | Saltiel | A41B 9/14 2/407 |
| 4,086,790 A | 5/1978 | Hanrahan et al. | |
| 5,131,100 A | 7/1992 | Atwater et al. | |
| 5,136,727 A | 8/1992 | Brisco | |
| 5,201,074 A | 4/1993 | Dicker | |
| 5,205,815 A | 4/1993 | Saunders | |
| 5,367,708 A | 11/1994 | Fujimoto | |
| 5,598,586 A | 2/1997 | Munjone | |
| 6,023,789 A | 2/2000 | Wilson et al. | |
| 6,146,240 A | 11/2000 | Morris | |
| 6,311,333 B1 | 11/2001 | Batra | |
| 6,401,250 B1 | 6/2002 | McNabb | |
| 6,430,752 B1 | 8/2002 | Bay | |
| 6,817,034 B2 | 11/2004 | Smilovic | |
| 6,874,337 B2 * | 4/2005 | Uno | A41D 1/08 2/401 |
| 7,631,367 B2 | 12/2009 | Caillibotte et al. | |
| 7,730,552 B2 | 6/2010 | Ota et al. | |
| 7,774,865 B2 | 8/2010 | Miller | |
| 2004/0111781 A1 | 6/2004 | Miyake et al. | |
| 2005/0229293 A1* | 10/2005 | Miller | A41B 9/02 2/403 |
| 2005/0229295 A1 | 10/2005 | Chun et al. | |
| 2005/0239370 A1 | 10/2005 | Oyama et al. | |
| 2005/0268379 A1 | 12/2005 | MacGeorge | |
| 2006/0130215 A1 | 6/2006 | Torry | |
| 2006/0169004 A1 | 8/2006 | Belluye et al. | |
| 2007/0022510 A1 | 2/2007 | Chapuis et al. | |
| 2007/0174950 A1 | 8/2007 | Gidish | |
| 2008/0244805 A1 | 10/2008 | Griffin | |
| 2009/0024069 A1 | 1/2009 | Appel | |
| 2009/0025115 A1 | 1/2009 | Duffy et al. | |
| 2009/0171259 A1 | 7/2009 | Soerensen et al. | |
| 2010/0113998 A1 | 5/2010 | Mizumoto | |
| 2010/0205713 A1* | 8/2010 | Takamoto | A41D 7/00 2/67 |
| 2011/0009793 A1 | 1/2011 | Lucero et al. | |
| 2011/0111932 A1 | 5/2011 | von Hoffmann et al. | |
| 2011/0237995 A1 | 9/2011 | Ota et al. | |
| 2013/0095730 A1 | 4/2013 | Jensen | |
| 2014/0082815 A1 | 3/2014 | Harber et al. | |
| 2014/0115747 A1 | 5/2014 | Spruill et al. | |
| 2014/0196196 A1 | 7/2014 | Lee | |
| 2014/0273743 A1 | 9/2014 | Hays et al. | |

FOREIGN PATENT DOCUMENTS

| | | | | |
|---|---|---|---|---|
| EP | 2181613 A1 * | 5/2010 | | A41C 1/02 |
| FR | 2996731 A1 | 4/2014 | | |
| GE | 985082 A | 3/1965 | | |
| JP | 10110306 A | 4/1998 | | |
| WO | 2008142334 A2 | 11/2011 | | |

OTHER PUBLICATIONS

Website Printout: "New Serola Sacroiliac Belt", MedSupports, Inc. (2 pages).

* cited by examiner

SUPPORT AND COMPRESSION GARMENTS

FIELD OF THE INVENTION

The present invention related to body garments and devices which provide a person with support to the body part on which the garment or device is worn. In particular, but not exclusively, the present invention relates to body garments which can be worn to provide support and compression during sport, pregnancy or recovery from an injury. However, it will be appreciated that the present invention has broader application and is not limited to these particular uses.

BACKGROUND OF THE INVENTION

Body muscles and joints can become sore or fatigued as a result of stresses from physical exertion, pregnancy or conditions such as pelvic instability or "Sloppy Pelvis" Syndrome, or Trendelenburg Sign, where one side of the hip drops down due to a weakness in the gluteus medius muscle.

A particular portion of the body prone to soreness and injury from the stresses of physical exertion and pregnancy is the lower back and pelvic region. The pelvis is the irregular bony structure located at the base of the spine. In the adult human, the pelvis is formed by the sacrum, the coccyx and a pair of hip bones. The hip bones are joined posteriorly to the sacrum and incorporate a socket portion receiving each leg.

The pelvis achieves its stability from rough joint surfaces, tough joint capsules and ligaments and muscles that cross over the joints. Damage to any of these structures can cause the pelvis to become unstable, resulting in pain and injury to the pelvis itself and/or nearby structures. Low back, pelvic and groin injuries primarily occur in sports, recreational and work activities that involve bending, twisting, changes in direction and/or speed and/or repetitive motions.

Pregnancy is a commonly recognised cause of pelvic instability. Relaxin is a hormone released during pregnancy to loosen the ligaments to prepare the pelvis for delivery of the baby. If a woman already has a degree of pelvic instability due to previous pregnancies, a pelvic or back injury and/or is generally very flexible, she may experience pain and dysfunction during her pregnancy and in extreme cases, difficulty walking that may require the use of crutches or a wheelchair. A woman may continue to experience problems related to pelvic instability for some time after giving birth.

Traditionally, elastic bands comprising hook and loop fasteners, such as Velcro® fasteners, are worn over the area to be supported. These bands are made of a breathable, elasticised material and are generally wide enough to provide good compression and support to the region on which it is worn. The bands are fastened in place using large Velcro® patches, straps or harness buckles. One disadvantage of these bands is that they are generally quite large and bulky with the degree of compression remaining the same throughout the entire band, which can be uncomfortable and awkward to wear. They are also unfashionable and can be an eyesore when they cannot be disguised underneath clothing. The material and thickness of the bands can also lead to chafing as a result of rubbing against the skin. While some bands incorporate an internal foam layer, they are still uncomfortable and unsightly to wear.

Various attempts have been made to alleviate these problems by providing body garments which provide integrated support for a user during sport activities. For example, U.S. Pat. No. 6,430,752 discloses sports shorts comprising diagonal elastics which crossover the pelvic region from the hip to the opposite mid-thigh in an arrangement which is duplicated on the front and the back of the shorts, to provide better support by mimicking the body's anterior and posterior diagonal sling systems. The waist area is circumferential to provide pelvic support. These shorts are not very resilient and are impractical to be worn during a game as they can still cause chafing. These shorts cannot be worn for sports such as Australian Rules Football, which require that compression shorts worn under football shorts must be flesh coloured.

Compressive and insulating sports shorts, such as those sold under the brand name Skins™ by SKINS North America LLC (www.skins.net), are designed to be worn under normal sports shorts. The sports shorts are cut to provide increased compression along the lateral rotator line and provide extra support to the deep buttock muscles. While these shorts aid in providing support and retain heat to provide speedy recovery for muscles, the degree of compression is often not sufficient to provide relief for most injuries or body ailments and cannot be targeted to specific regions.

Support shorts, referred to as Post-Pregnancy Recovery Shorts and Post-Pregnancy Sports Shorts in the marketplace, are designed to provide support to the upper abdomen, caesarean wounds and the perineum. However, these shorts are only suitable for use after giving birth and do not provide the necessary support for the lower lumbar region and pelvic region required during pregnancy.

Sacroiliac joint belts, such as the Serola Sacroiliac Belt (sold by MedSupports, Inc., www.serola.net), have been designed to compress and support the sacroiliac joint, which is a common factor causing lower back pain. These types of belts are often prescribed by physiotherapists, and others, to patients with pelvic instability as an adjunct to treatment. Compression is applied transversely through the pelvis by the belt to mimic the stabilising action of the transversus abdominus muscle and the multifidus muscle. Some of the disadvantages with these belts are that they are uncomfortable to wear and can press against or cut into the stomach when the wearer sits down. For women having weight gain during or after pregnancy, the belt may produce unsightly bulges above and below the belt that are difficult to disguise under clothing. It is also difficult to maintain the belts in the correct place as they exhibit a tendency to ride up and down. The sacroiliac joint belts are also not able to be worn during sport as they are too cumbersome and are potentially dangerous to opponents during contact sports. An alternative is to apply a compressive tape to the pelvis for wear during sport; however, this is not suitable for those players allergic to sports tape. A knowledgeable and skilled person is also generally required for correct application of tape.

OBJECTS OF THE INVENTION

It is a preferred object of the invention to provide a support and compression garment that addresses or ameliorates one or more of the aforementioned problems of the prior art or provides a commercial alternative.

It is a preferred object of the invention to provide a support and compression garment which provides support to at least one targeted region of a person's body.

It is a further preferred object of the invention to provide a support and compression garment which is comfortable for a user to wear.

SUMMARY OF THE INVENTION

Generally, the present invention relates to a support and compression garment which provides support and compression targeted to a region of a person's body.

According to one aspect, although not necessarily the broadest aspect, the present invention resides in a support and compression garment comprising:

a body comprising at least one support and compression portion for providing support and compression to at least one targeted region of a person's body; and at least one support and compression member associated with the at least one support and compression portion for increasing the amount of support and compression.

Preferably, the support and compression garment is in the form of a short pant, but may also be in the form of a long pant.

Preferably, the support and compression garment further comprises a leg portion having a pair of legs for receiving at least a person' thighs.

Preferably, the leg portion has a ribbed edging which extends along an inner side of the pair of legs and/or an inbuilt gusset.

Preferably, the body comprises a waistband.

Preferably, the at least one support and compression portion is specifically positioned over or integrally formed with the waistband.

Preferably, the waistband comprises at least one attachment member for allowing the support and compression member to be connected to the support and compression portion.

Suitably, the at least one support and compression portion is made of a ribbing material having a 2×2 ribbing profile.

Suitably, the material of the support and compression portion has a sufficient elastane content for providing the appropriate degree of support and compression to the targeted region.

Suitably, the support and compression member is in the form of a support and compression belt.

Suitably, the support and compression belt has at least one hook portion and at least one loop portion for fastening the support and compression belt about the waistband.

Suitably, the support and compression belt is integrated within the waistband of the garment.

Suitably, the body of the garment is elongated.

Preferably, the length of the elongated body can be varied to accommodate a person's stomach enlarging during pregnancy.

Preferably, the support and compression portion is specifically positioned over a waistband of the elongated body of the garment to provide support and compression to the stomach and pelvic region.

Preferably, the body comprises a central region positioned over the middle of the stomach which is made of a material having zero elasticity content or an elasticity content lower than that of the support and compression portion, to avoid excessive support and compression being applied directly onto the baby.

Suitably, the garment is made of a comfortable fabric material.

Suitably, in an embodiment having leg portions extending over the thigh, the body includes support and compression portions having a moderate compression level associated at least with respective selected thigh muscle groups.

Suitably, in an embodiment having leg portions extending to the ankle, the body includes support and compression portions having a light compression level, associated at least with respective gastrocnemius muscles.

Suitably, the support and compression garment includes a waistband and at least one support and compression portion and the waistband and support and compression portion comprise ribbing material having a ribbing profile and the ribbing profile of the ribbing material of the support and compression portion is integrally formed with the ribbing profile of the ribbing material of the waistband.

Further aspects and features of the present invention will become apparent from the following detailed description.

BRIEF DESCRIPTION OF THE DRAWINGS

By way of example only, preferred embodiments of the invention will be described more fully hereinafter with reference to the accompanying drawings, wherein:

FIG. 1d is plan view of a support and compression belt for use with the garment in FIG. 1a;

FIG. 4b is a front view of an alternative embodiment of the support and compression garment in FIG. 4a;

FIG. 5a is a front view of an additional embodiment of the support and compression garment of FIG. 1a;

FIG. 6b is a rear view of the support and compression garment of FIG. 6a.

DETAILED DESCRIPTION OF THE PREFERRED EMBODIMENTS

Figure 1A:
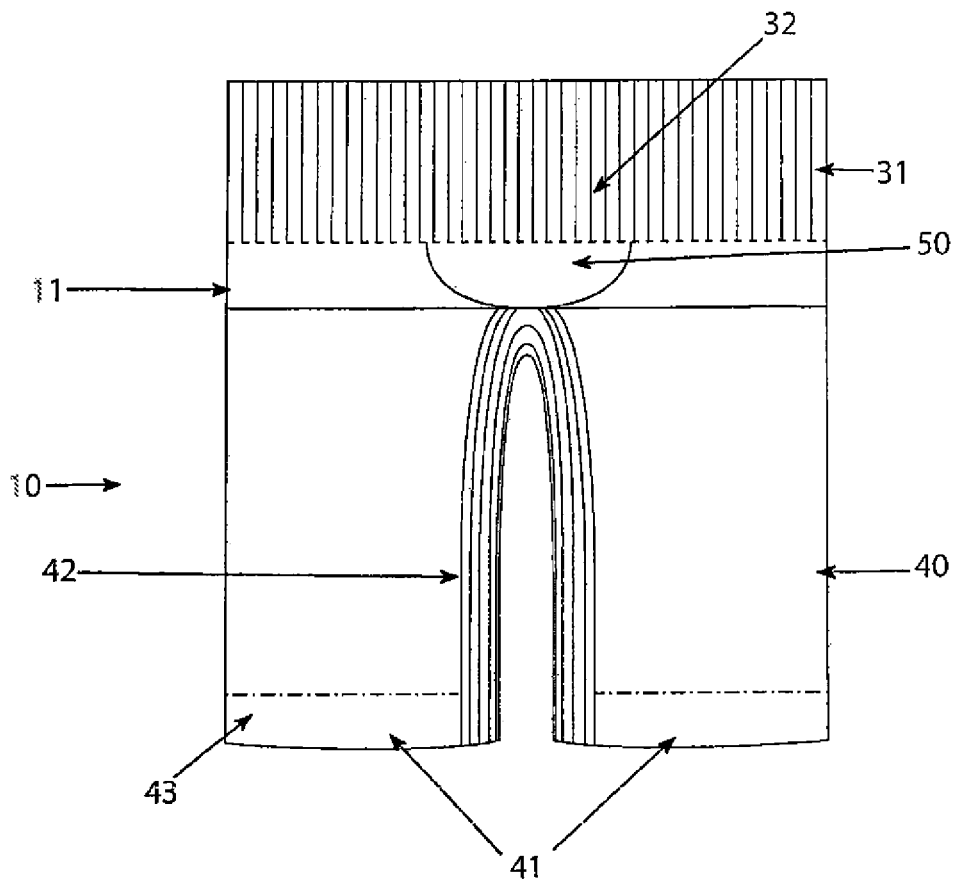
FIG. 1a is a front view of a support and compression garment for core support.

Preferred embodiments of a support and compression garment of the present invention are shown in the Figures and generally designated by the reference numeral 10 shown in FIG. 1a. According to some embodiments illustrated herein, the support and compression garment 10 is in the form of a short pant for providing support and compression to at least one targeted region of a person's body and in particular, a person's lumbar and/or pelvic and/or abdominal regions. In alternative embodiments, the garment 10 can be elongated to be in the form of three-quarter length or full length pants or leggings. The garment 10 could also be in the form of a three-quarter or full body garment. Preferably, the garment 10 is made of a fabric material commonly used for clothing which is comfortable against a person's skin, suitable for long-term wear and aesthetically pleasing. For example, the garment can be made of any suitable synthetic or natural fibre or other material. Alternatively, the garment can also be made of a wood pulp or bamboo fibre material.

As shown in FIG. 1a, the support and compression garment 10 comprises a body 11 and a leg portion 40. According to some embodiments, the leg portion 40 is integrally formed with a base of the body 11 and comprises a pair of legs 41 to be received over a person's thighs. A hem 43 is provided along the bottom edge of the legs 41. In alternative embodiments, the length of the pair of legs 41 can be varied as desired to cover more or less of a person's legs. For example, the garment 10 can have shorter length legs 41 to be more comfortable for a person to wear in summer. Preferably, the leg portion 40 has a ribbed edging 42 which extends along an inner side of the pair of legs 41 and gusset 50. The ribbed edging 42 preferably comprises a 1×1 ribbing profile so that the legs 41 will be contoured to the person's thighs and have a reduced degree of support and compression compared to that of a support and compression portion 32 for added comfort and long-term wear.

Preferably, the leg portion 40 has an integrated gusset 50 for supporting a person's groin area while wearing the support and compression garment 10. It is envisaged that the inbuilt gusset 50 can be tailored in different embodiments of the garment 10 to suit a male or female. The inbuilt gusset 50 is preferably made of a breathable material which can be same as, or different from, the material of the leg portion 40 for hygiene purposes. In a further embodiment of the present invention, the integrated gusset 50 can be omitted in a female version of the support and compression garment 10, as illustrated in FIG. 1b.

Figure 1B:
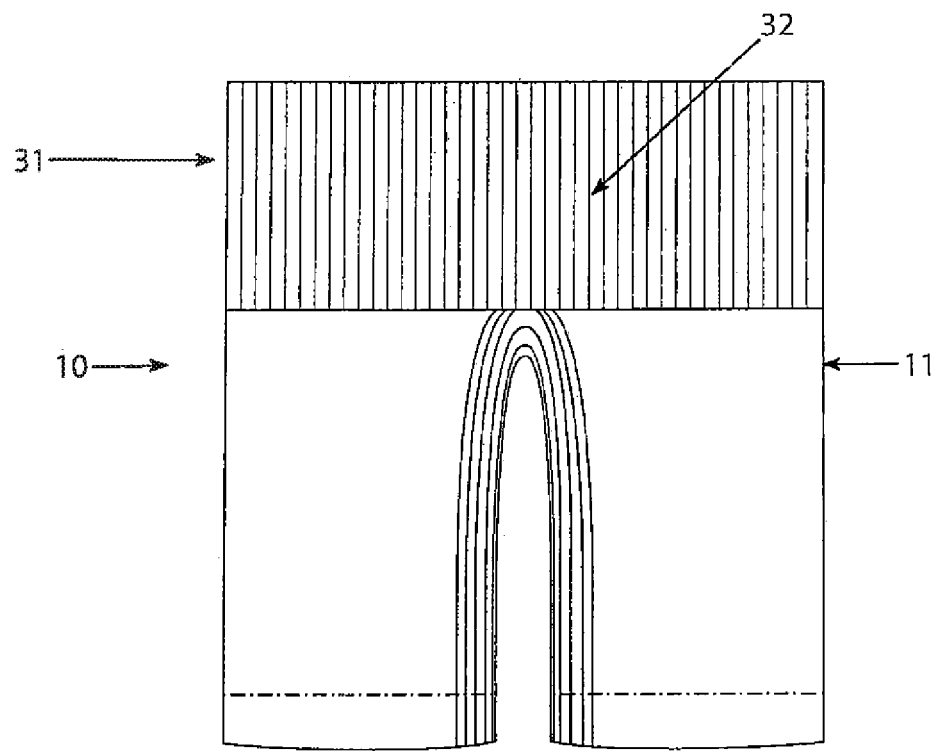
FIG. 1b is a front view of an alternate version of the support and compression garment of the support and compression garment of FIG. 1a to be worn by a female.

FIGS. 1a and 1b show the support and compression garment 10 in the form of a core short pant for providing support and compression to a core region of a person. As illustrated, the support and compression garment 10 comprises the body 11 having at least one support and compression portion 32 for providing support and compression to a targeted region of a person's body, such as the abdominal muscles in the front and the thoraco-lumbar muscles of the lower back. The support and compression portion 32 shown in FIGS. 1a and 1b, is specifically positioned over or integrally formed with a waistband 31 on the body 11 of the garment 10 to provide support and compression to a targeted area namely, the core region. In an alternative embodiment, it is envisaged that a hem can be provided on the waistband 31 for receiving an elastic member or the like to assist in holding a top edge of the garment about a person's waist.

Preferably, the support and compression portion 32 is made of a ribbing material having a 2×2 ribbing profile (or weaving of two side-by-side threads crossing two side-by-side threads). The 2×2 ribbing profile provides sufficient elasticity to provide the necessary support and compression for the support and compression portion 32. Preferably, the support and compression portion 32 will have eighteen percent (by weight) elastane (or spandex) content (a polyurethane-polyurea co-polymer) or other suitable amount for providing sufficient compression. An example material for high support and compression can comprise about 65% (by weight) polyamide, 25% spandex and 10% polyester Alternatively, the support and compression portion 32 can have a different ribbing profile or be made of a different material to increase or decrease the support and compression of the support and compression portion 32 as required.

Figure 1C:
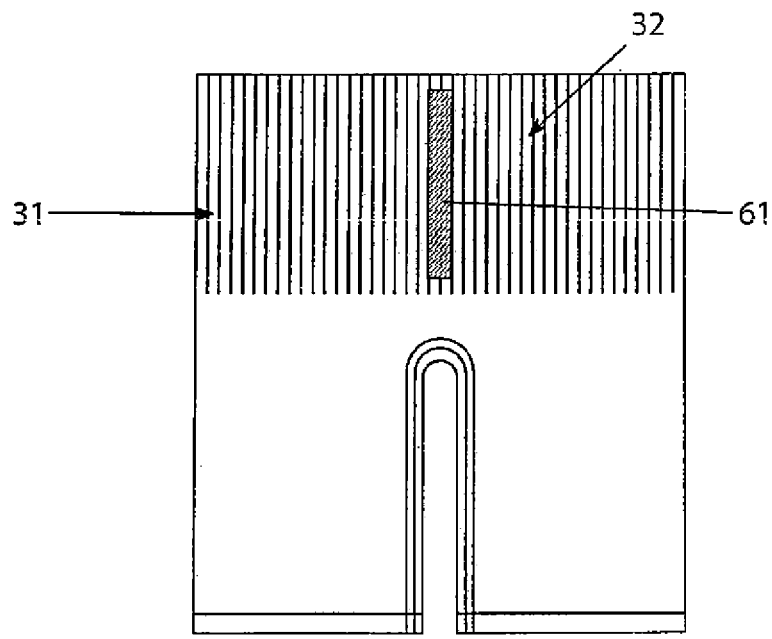
FIG. 1c is a rear view of the support and compression garment in FIG. 1a showing an attachment member.

The support and compression portion 32 preferably extends around a rear side of the support and compression garment as illustrated in FIG. 1c attached to the garment such as by stitching or another conventional method. According to some embodiments shown in FIG. 1c, the garment 10 comprises an attachment member 61. Preferably, the attachment member 61 is located on a rear side of the waistband 31 and positioned at a suitable point on the support and compression portion 32. In the embodiment shown in FIG. 1c, the attachment member 61 is in the form of a strip of hooks or loops for attachment via a hook and loop fastener mechanism, such as Velcro® fasteners. Preferably, the attachment member 61 comprises a dense layer of loops and is vertically oriented and positioned substantially centrally on the rear side of the waistband 31 for receiving a support and compression member 70 shown in FIG. 1d. Attachment member 61 may be attached to the garment by stitching or another conventional method.

Figure 1D:
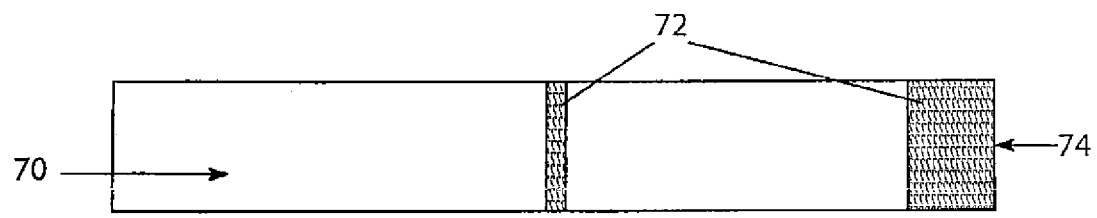

As illustrated in FIG. 1d, the support and compression member 70 is in the form of a support and compression belt. Preferably, the support and compression belt 70 is made of a stretch elastic material suitable for providing additional support and compression for the support and compression portion 32. The length of the support and compression belt can be varied to fit around a person's waist and can be made in different lengths or be adjustable. A top side of the belt comprises at least one hook portion 72 comprising a dense layer of hooks. Preferably, a first hook portion 72 is positioned substantially centrally on the top side of the support and compression belt 70 for attaching the support and compression belt 70 to the attachment member 61 of the waistband 31. A second hook portion 72 is provided on a first end 74 of the support and compression belt 70.

Figure 1E:
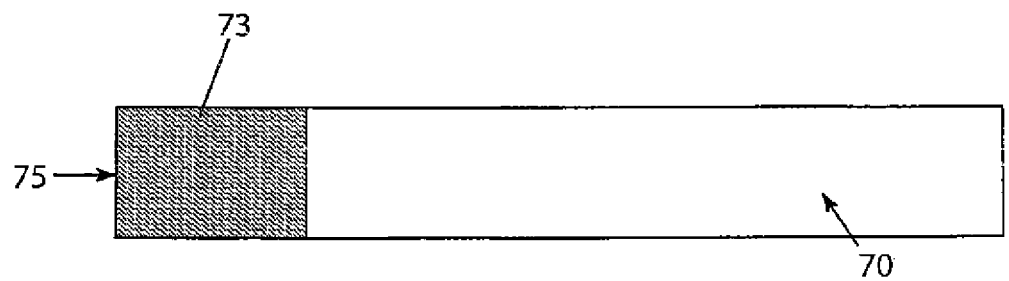
FIG. 1e is an underneath view of the support and compression belt in FIG. 1c.

A bottom side of the belt 70 shown in FIG. 1e, comprises a loop portion 73 comprising a dense layer of loops on a second end 75 of the support and compression belt 70 for allowing the first end 74 of the belt to be connected to the second end 75 by attaching the loop portion 73 to the hook portion 72 on the first end 74. In an alternative embodiment of the support and compression belt, it will be acknowledged that the positioning of the hook and loop portions may be varied as desired. In further alternative embodiments, the hook and loop fastening mechanism can be replaced with any other suitable fastening mechanism.

Figure 2A:
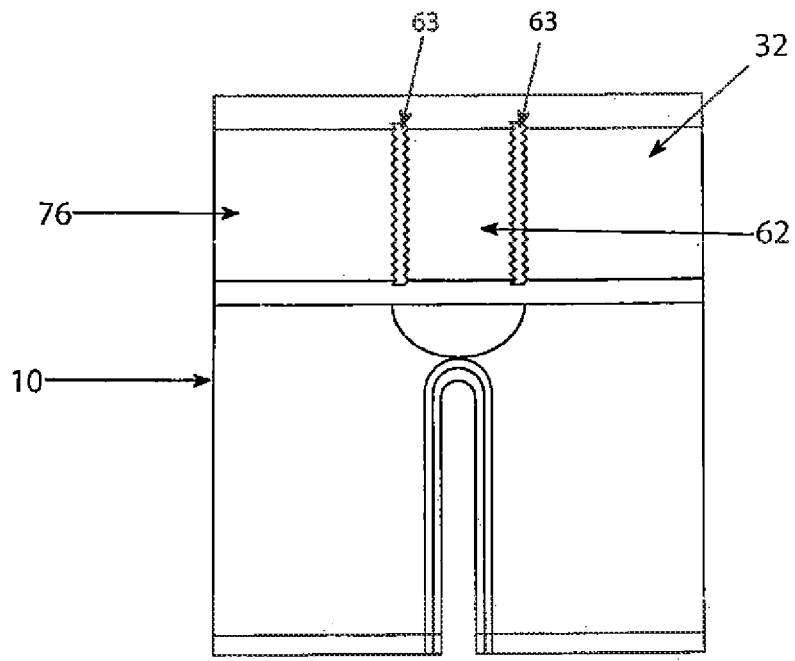
FIG. 2a is a front view of an alternative embodiment of the support and compression garment in FIG. 1a to be worn during sport.

FIG. 2a illustrates an alternative embodiment of the support and compression garment 10 to provide support and compression during sport comprising an alternative attachment section 62 located on the front side of the garment 10. Preferably, the attachment section 62 is in the form of at least one aperture 63. As shown in FIG. 2a, there are two apertures 63 stitched into the waistband 31 that are vertically orientated and positioned substantially centrally on the waistband 31. The apertures 63 are suitably spaced apart so that a support and compression belt 70 can be threaded through the apertures 63 and be secured over the waistband, providing additional support and compression for the support and compression portion 32 on the waistband 31.

Figure 2B:
FIG. 2b is a plan view of an alternative embodiment of the support and compression belt in FIG. 1c.
Figure 2C:
FIG. 2c is an underneath view of the support and compression belt in FIG. 2b.

Referring now to FIG. 2b showing an alternative support and compression belt 76, a top side of the support and compression belt 76 comprises a hook portion 72 provided on the first end 74 of the support and compression belt 76. A bottom side of the support and compression belt 76 shown in FIG. 2c, comprises a loop portion 73 comprising a dense layer of loops on the second end 75 of the support and compression belt 76 for allowing the first end 74 of the support and compression belt 76 to be connected to the second end 75 by attaching the loop portion 73 to the hook portion 72.

Figure 3:
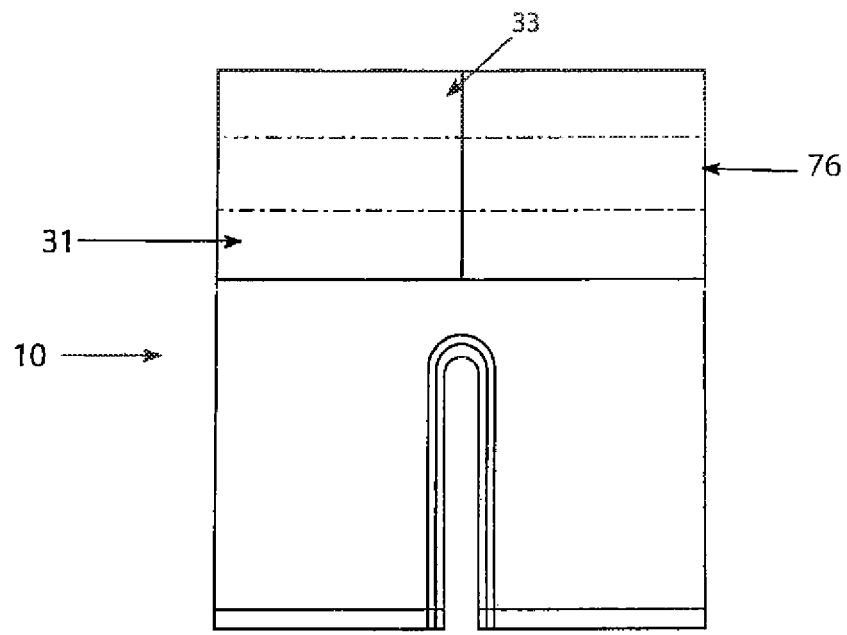
FIG. 3 is a front view of an alternative embodiment of the support and compression garment in FIG. 2a having an integrated support and compression belt.

In an alternative embodiment of support and compression garment 10, the support and compression belt 76 is integrated so that it is concealed to prevent the belt 76 being ripped off or loosened during sport. The rear side of the support and compression garment 10 having an integrated compression belt 76 is illustrated in FIG. 3. Preferably, the waistband 31 can comprise an aperture 33 for allowing the compression belt to be inserted into or removed from the waistband 31, or to provide access for adjustment of the compression belt as desired. Alternatively, the support and compression belt 76 may be permanently inserted within the waistband 31 during manufacture of the garment 10 via stitching or the like.

Figure 4A:
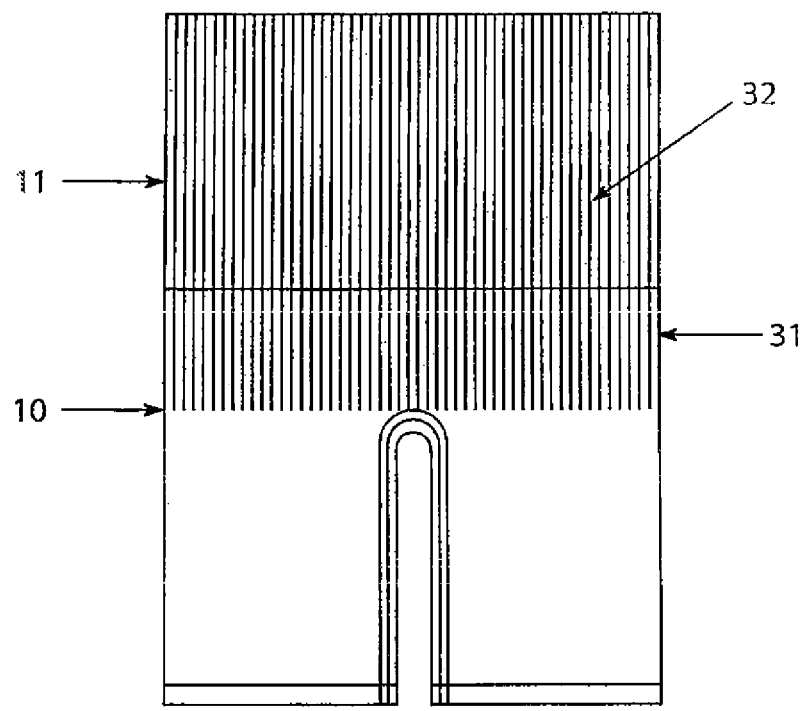
FIG. 4a is a front view of a further alternative embodiment of the support and compression garment in FIG. 1a to be worn during pregnancy.
Figure 4B:
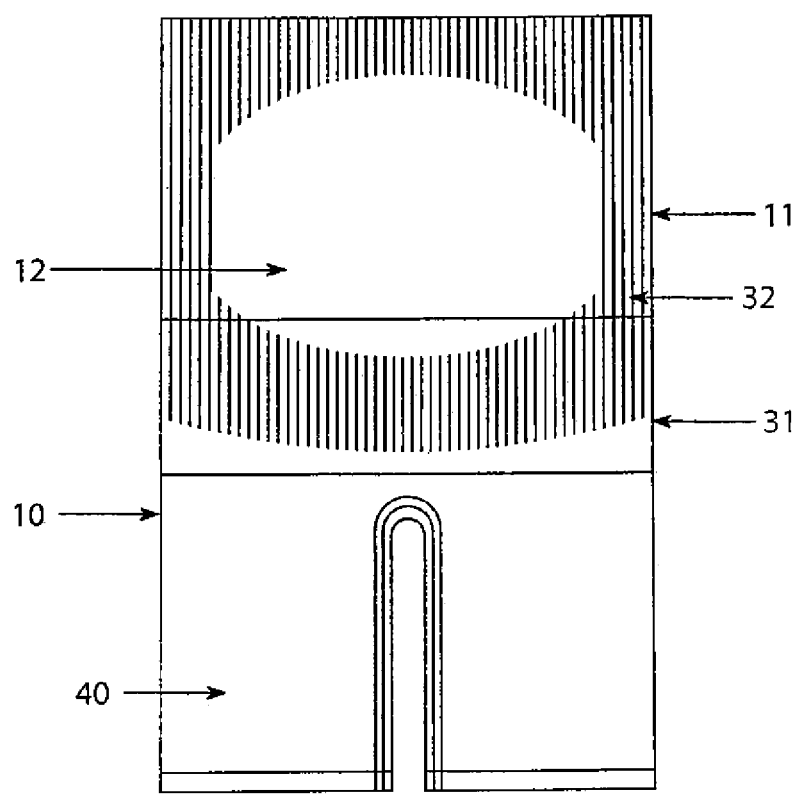
Figure 4C:
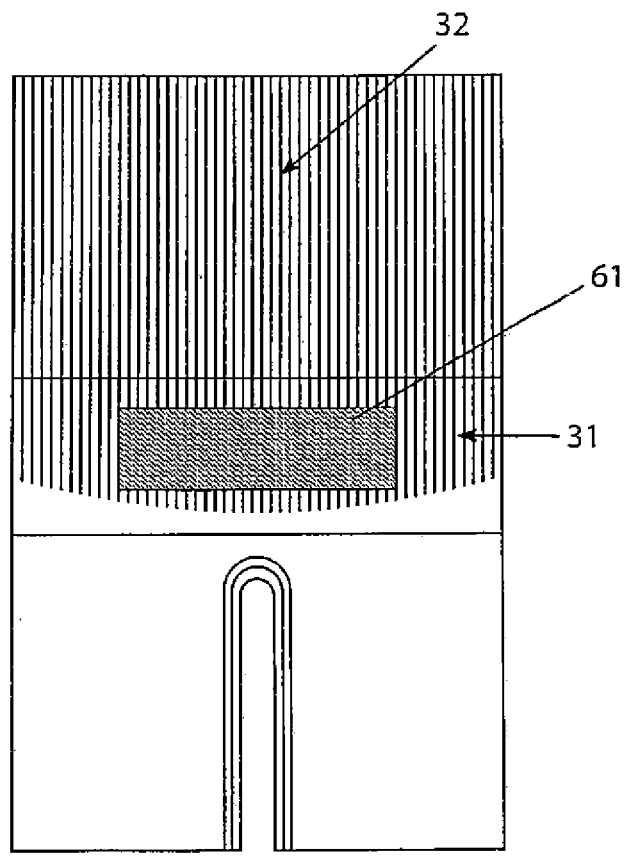
FIG. 4c is a rear view of the support and compression garment in FIGS. 4a and 4b.

FIGS. 4a to 4c illustrate alternative embodiments of the support and compression garment 10 to provide pelvic support during pregnancy. Preferably, the body 11 of the compression garment 10 is elongated to cover and provide support over a person's stomach. The length of the body 11 can be varied to accommodate the stomach enlarging during pregnancy. For example, the body 11 can be folded inwardly or outwardly until a desired length is obtained. The material of the garment 10 ensures that the folded section will not become excessively bulky. As illustrated in FIG. 4a, the support and compression portion 32 is specifically positioned over the waistband 31 and the body 11 of the garment 10 to provide support and compression to the stomach and pelvic regions.

In an alternative embodiment shown in FIG. 4b, a central region 12 which lies over the middle of the stomach is made of a material having zero elasticity content or an elasticity content lower than that of the support and compression portion 32, to avoid excessive support and compression being applied directly onto the baby. The material can be the same as, or different from, the material used for the leg portion 40 of the garment 10. The support and compression portion 32 is specifically positioned over the waistband 31 and the body 11 surrounding the central region 12.

The support and compression portion 32 for the embodiments shown in FIGS. 4a and 4b preferably extends around the back side of the support and compression garment as illustrated in FIG. 4c. As shown in FIG. 4c, the garment comprises a larger version of the attachment member 61 horizontally oriented on the waistband 31 for providing lumbar support.

Figure 4D:
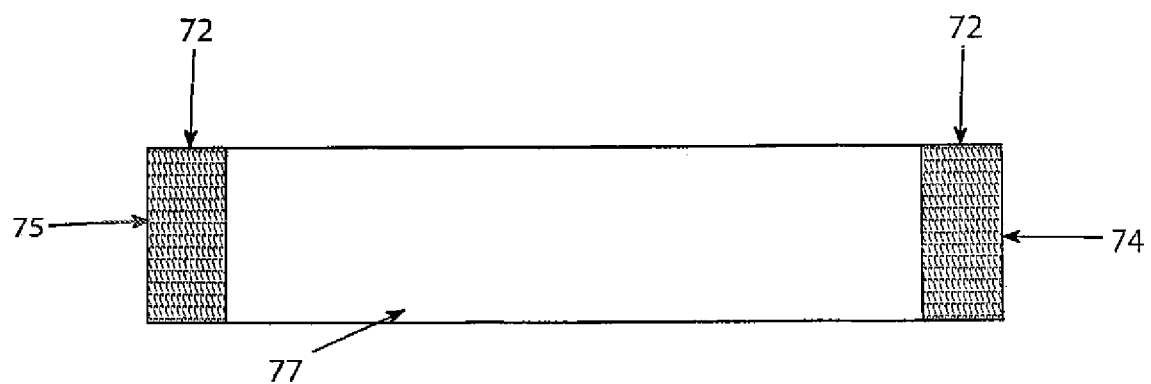
FIG. 4d is a plan view of a further alternative embodiment of the support and compression belt in FIG. 1d.

FIG. 4d shown an alternative support and compression belt 77 for the use during pregnancy. Preferably, the support and compression belt 77 comprises a pair of hook portions 72, wherein one hook portion 72 is provided on the first end 74 and another hook portion 72 is provided on a second end 75 of the support and compression belt 77, to be attached to the attachment member 61 on the waistband 31 for providing additional support and compression.

Figure 5A:
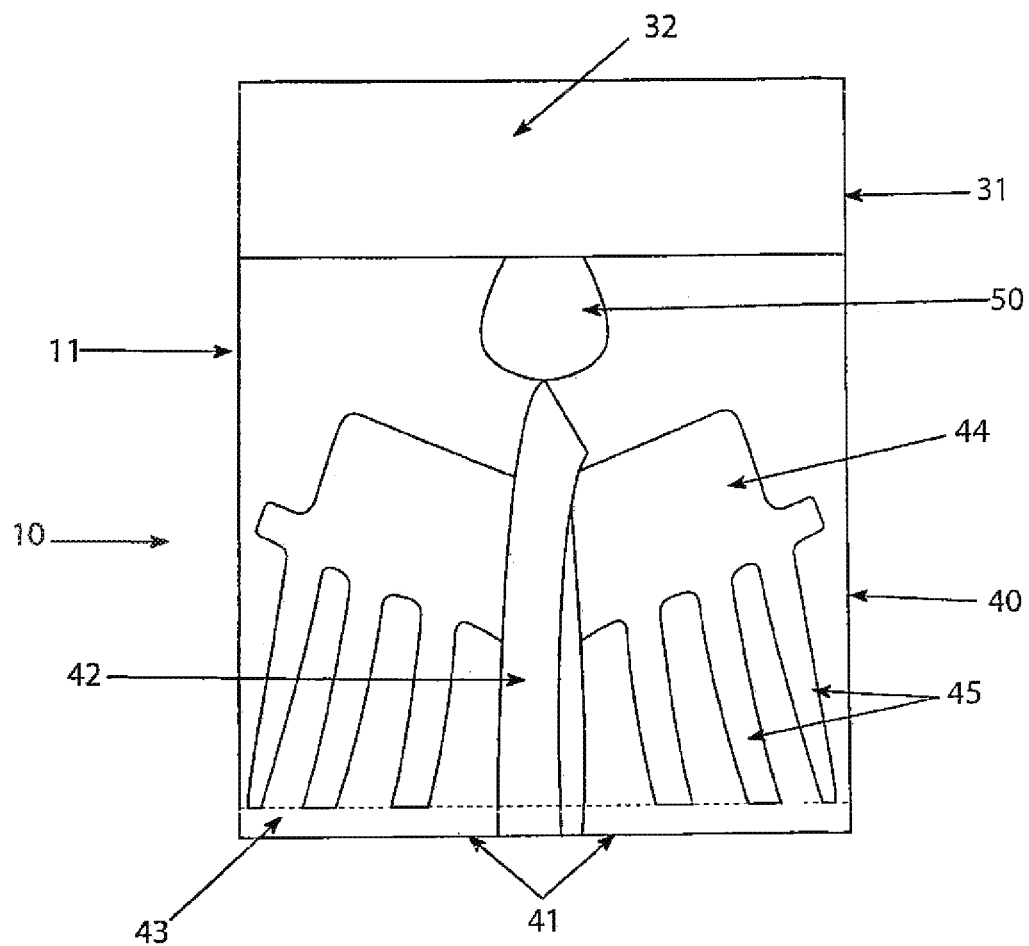
Figure 5B:
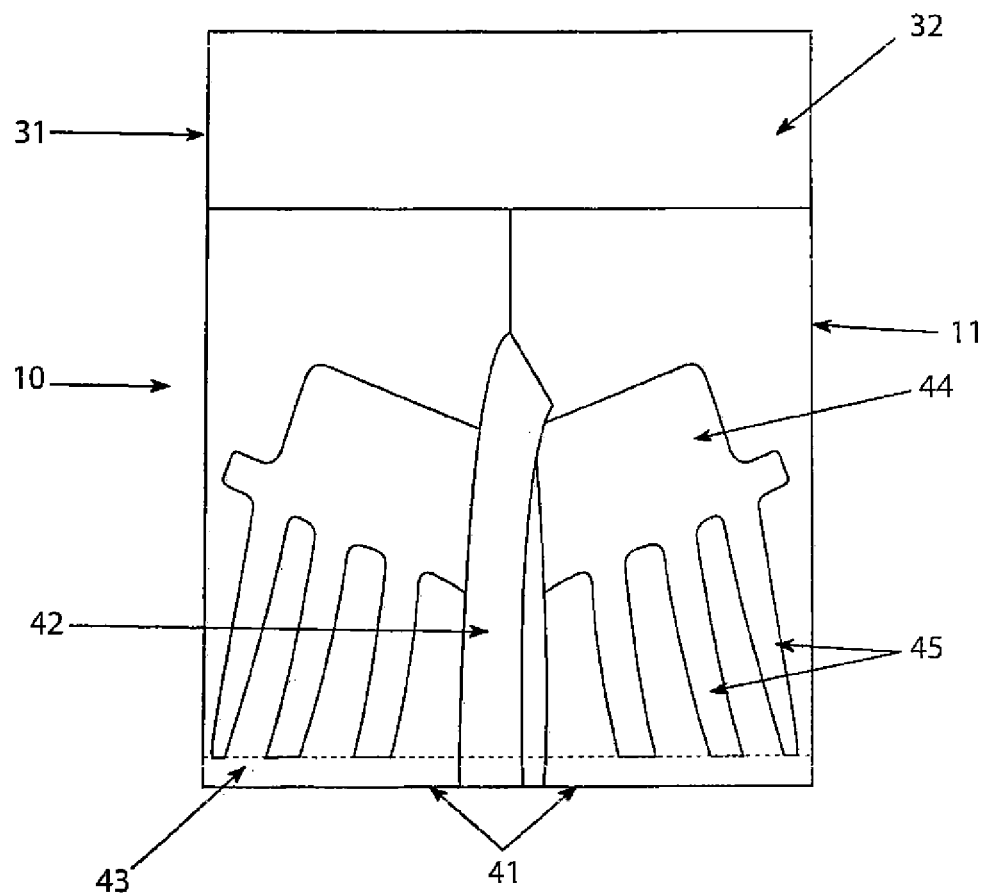
FIG. 5b is a rear view of the support and compression garment of FIG. 5b.

In FIGS. 5a and 5b, garment 10 is shown to have a body 11, a waistband 31 and at least one support and compression portion 32 associated with the abdominal and pelvic region, as in FIG. 1a. The leg portion 40 is shown to include a pair of legs 41 for covering the thigh, each leg 41 having a ribbing edge 42 and a hem 43, and also a gusset 50 (FIG. 5a). Additionally, garment 10 includes strategically engineered support and compression portions 44 associated with the upper thighs from which extend a plurality of extended portions 45 associated with respective targeted muscle groups, such as the rectus femoris and sartorius muscles in the front, and (not shown) similar portions and extensions associated with the biceps femoris and gluteus maxim us muscles in the rear. These portions 44, 45 are preferably of moderate compression levels, and provide protection especially against extensive vibration during a workout or playing sport. Such body mapping also facilitates lower body muscle groups in fast recovery after heavy workout or competition. An example material for moderate support and compression could be about 70% (by weight) polyamide, 15% spandex and 15% polyester.

Figure 6A:
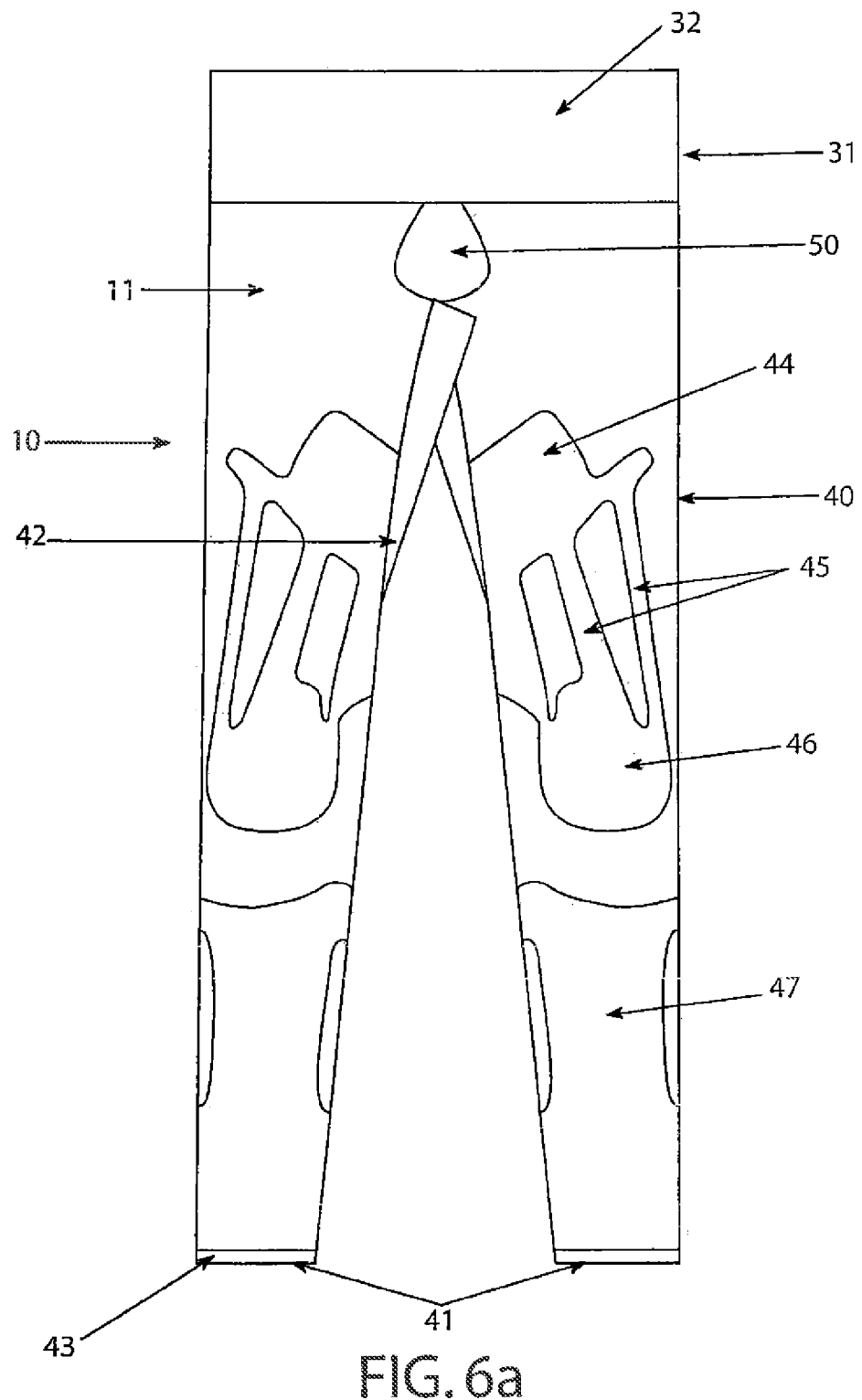
FIG. 6a is a front view of yet a further embodiment of the support and compression garment of FIG. 1a having full leg length.
Figure 6B:
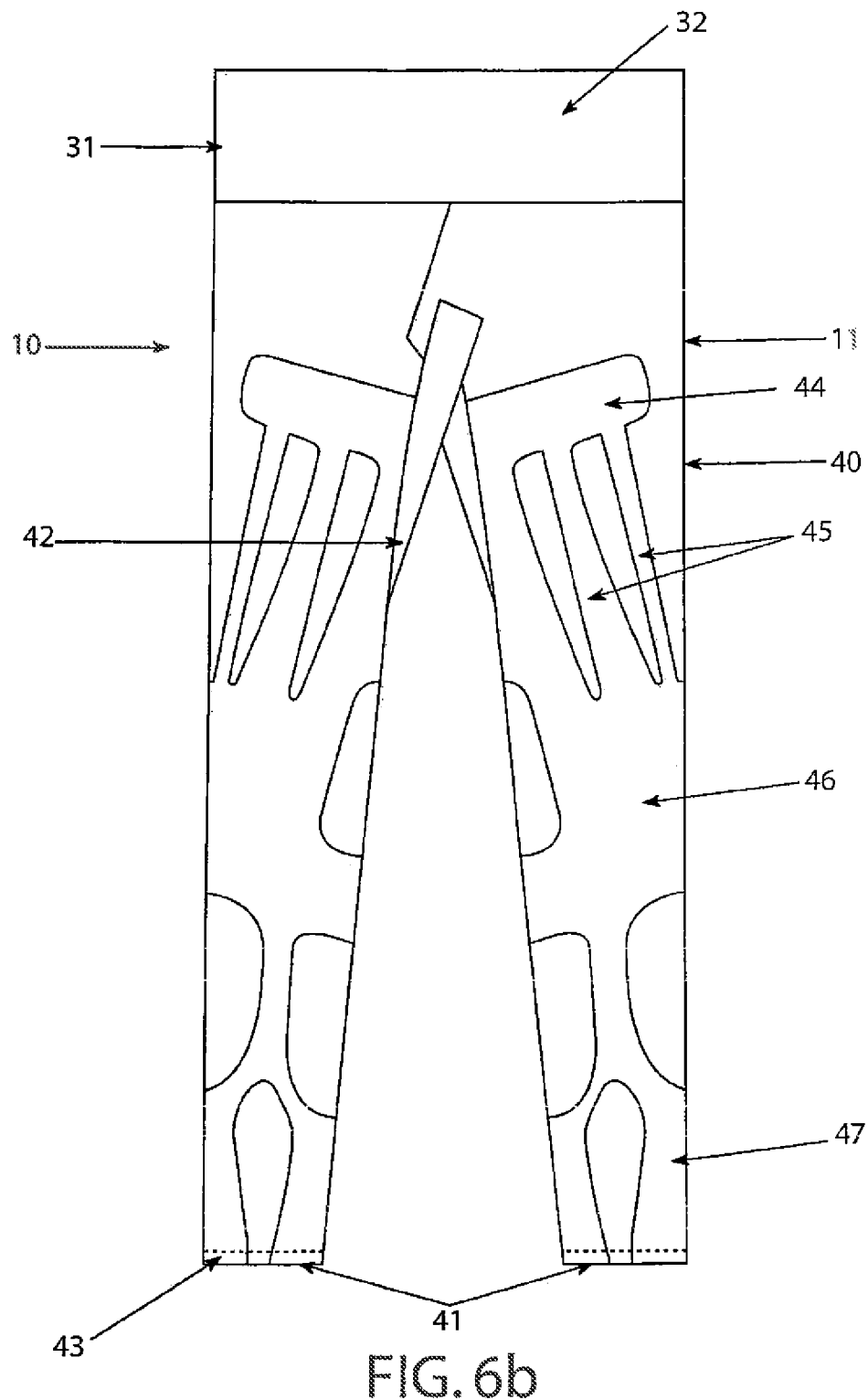

In FIGS. 6a and 6b, garment 10 is shown to have a body 11, a waistband 31 and at least one support and compression portion 32 associated with the abdominal and pelvic region, as in FIG. 1a. The leg portion 40 is shown to include a pair of legs 41 for covering the thigh, each leg 41 having a ribbing edge 42 and a hem 43, and also a gusset 50 (FIG. 6a). Garment 10 includes strategically engineered support and compression portions 44 associated with the upper thighs from which extend a plurality of extended portions 45 associated with respective targeted muscle groups, with portions 44, 45 having moderate compression levels as with the garments of FIGS. 5a and 5b. Additionally, garment 10 of FIGS. 6a and 6b includes strategically engineered support and compression portions 46 associated with the knee region, and also include portions 47 associated with targeted muscle groups of the calf region, including gastrocnemius muscles. Portions 46, 47 may preferably have fight compression levels. As with the garment of FIGS. 5a and 5b, portions 46, 47 provide protection especially against extensive vibration during a workout or playing sport and also facilitate lower body muscle groups in fast recovery after heavy workout or competition. An example material for light support and compression could be similar in content to that for moderate support and compression but have a different knitting method, as is known.

Hence, the present invention provides a solution for alleviating the problems of the prior art by providing a support and compression garment which is comfortable, aesthetically pleasing, able to provide support and compression to targeted areas and does not required technical expertise to be fitted. The support and compression garment is able to replicate the body's own deep stabilising system by providing optimal placement of external compressive forces through the pelvic region. Embodiments of the support and compression garment can also be used during sport. The detachable support and compression member and its variable positioning of some embodiments allow the wearer to vary the degree and/or location of compression, for example, as the wearer recovers from an injury, becomes more heavily pregnant and/or needs more support when engaging in strenuous activities such as housework, lifting or gardening. Generally, overall the support and compression composition is 68% (by weight) polyamide, 18% spandex, and 14% polyester.

Throughout the specification, the aim has been to describe the preferred embodiments of the invention without limiting the invention to any one embodiment or specific collection of features. It is to be appreciated by those of skill in the art that, various modifications and changes can be made in the particular embodiments exemplified without departing from the scope of the claims or the spirit of the present invention.

What is claimed is:

1. A support and compression garment configured to stabilize a pelvis and a lumbar region of a wearer, the support and compression garment comprising:

a body portion comprising a waistband at an upper location of the body portion, a mid portion adapted to fit over an abdomen, the pelvis and the lumbar region of the wearer, and a leg portion extending down from a lower portion of the body portion;

the leg portion having a pair of legs for receiving respective thighs of the wearer; the body portion comprising at least one support and compression portion extending downward from and defining an uppermost edge of the support and compression garment, extending through the mid portion, and further extending to the leg portion, the at least one support and compression portion adapted to provide support and compression to the abdomen, the pelvis and the lumbar region of the wearer and adapted to stabilize the pelvis and the lumbar region of the wearer, the at least one support and compression portion and the waistband are entirely made of a ribbing material having a ribbing profile, the ribbing profile of the ribbing material of the at least one support and compression portion is integrally formed with the ribbing profile of the ribbing material of the waistband and forming a continuous ribbed surface of the body portion, extending from the uppermost edge of the support and compression garment to the leg portion, the ribbing material of the at least one support and compression portion extending around the waistband and covering the wearer's pelvis and lumbar region, in use, to provide support and compression to the wearer's pelvis and lumbar region to improve pelvic stability.

2. The support and compression garment as claimed in claim 1, wherein the support and compression garment is in the form of a short pant.

3. The support and compression garment as claimed in claim 1, wherein the garment includes an inbuilt gusset, wherein the leg portion has a ribbed edging which either extends along an inner side of the pair of legs or extends along the inbuilt gusset of the support and compression garment.

4. The support and compression garment as claimed in claim 1, wherein the ribbing profile of the ribbing material of the at least one support and compression portion and the ribbing material of the waistband is a 2×2 ribbing profile.

5. The support and compression garment as claimed in claim 1, further comprising at least one support and compression member removably attachable to the at least one support and compression portion for increasing the amount of support and compression.

6. The support and compression garment as claimed in claim 5, wherein the waistband further comprises at least one attachment member for allowing the at least one support and compression member to be connected to the at least one support and compression portion.

7. The support and compression garment as claimed in claim 5, wherein the at least one support and compression member is in the form of a support and compression belt.

8. The support and compression garment as claimed in claim 7, wherein the support and compression belt has at least one hook portion and at least one loop portion for fastening the support and compression belt about the waistband.

9. The support and compression garment as claimed in claim 1, wherein the at least one support and compression portion is made of a material comprising about 65% (by weight) polyamide, 25% spandex and 10% polyester.

10. The support and compression garment as claimed in claim 1, wherein the leg portion is integrally formed with the lower portion of the body portion.

* * * * *